US011660401B2

(12) United States Patent
Cohen (10) Patent No.: US 11,660,401 B2
(45) Date of Patent: May 30, 2023

(54) DRUG DELIVERY DEVICE WITH NON-CONTACT SENSOR (71) Applicant: SANOFI, Paris (FR)

(72) Inventor: Nadav Cohen, Tirat Carmel (IL)

(73) Assignee: Sanofi, Paris (FR)

( * ) Notice: Subject to any disclaimer, the term of this patent is extended or adjusted under 35 U.S.C. 154(b) by 357 days.

(21) Appl. No.: 16/955,316

(22) PCT Filed: Dec. 18, 2018

(86) PCT No.: PCT/EP2018/085389
§ 371 (c)(1),
(2) Date: Jun. 18, 2020

(87) PCT Pub. No.: WO2019/121610
PCT Pub. Date: Jun. 27, 2019

(65) Prior Publication Data
US 2021/0016014 A1 Jan. 21, 2021

(30) Foreign Application Priority Data

Dec. 21, 2017 (EP) ..................................... 17306871

(51) Int. Cl.
A61M 5/315 (2006.01)

(52) U.S. Cl.
CPC ...... *A61M 5/31568* (2013.01); *A61M 5/3159* (2013.01); *A61M 5/31525* (2013.01);
(Continued)

(58) Field of Classification Search
CPC ...... A61M 5/31568; A61M 2205/3317; A61M 5/3159; A61M 2205/3327; A61M 5/178;
(Continued)

(56) References Cited

U.S. PATENT DOCUMENTS 5,536,249 A 7/1996 Castellano et al.
5,582,598 A 12/1996 Chanoch
(Continued)

FOREIGN PATENT DOCUMENTS

EP 1361908 11/2003
EP 1361908 A1 * 11/2003 ............ A61M 5/142
(Continued)

OTHER PUBLICATIONS

Mizukami, Magnetism Sensor Nov. 5, 1998—Machine Translation of the JP11304893A (Year: 1998).*
(Continued)

*Primary Examiner* — Katherine H Schwiker
*Assistant Examiner* — Robert F Allen
(74) *Attorney, Agent, or Firm* — Fish & Richardson P.C.

(57) ABSTRACT

A drug delivery device includes a magnet assembly, a coil assembly and processing circuitry. The magnet assembly has a plurality of magnets arranged in a ring. The coil assembly has one or more coils. The magnet assembly and the coil assembly are arranged to rotate relative to each other during ejection of medicament from the drug delivery device such that a voltage signal is produced in the coil assembly when a unit of dose is ejected. The processing circuitry is arranged to: receive the voltage signal; increment a counter in response to receipt of the voltage signal; and store information indicative of the number of units of dose ejected during a medicament ejection.

18 Claims, 7 Drawing Sheets (52) U.S. Cl.
CPC . *A61M 5/31575* (2013.01); *A61M 2205/3317* (2013.01); *A61M 2205/3327* (2013.01); *A61M 2205/52* (2013.01)

(58) Field of Classification Search
CPC ............ A61M 5/31525; A61M 5/3139; A61M 5/31526; A61M 5/31528; A61M 5/31545; A61M 5/31546; A61M 5/31548; A61M 5/3155; A61M 5/31551; A61M 5/31553; A61M 5/31556; A61M 5/31558
See application file for complete search history.

(56) References Cited

U.S. PATENT DOCUMENTS

| | | | |
|---|---|---|---|
| 6,482,185 | B1 | 11/2002 | Hartmann |
| 11,318,251 | B2 | 5/2022 | Miller et al. |
| 11,426,527 | B2 | 8/2022 | Byerly et al. |
| 2002/0143288 | A1 | 10/2002 | Larsen et al. |
| 2003/0055685 | A1 | 3/2003 | Cobb et al. |
| 2006/0161112 | A1* | 7/2006 | Steffen ............... G01D 5/145 604/188 |
| 2006/0175427 | A1 | 8/2006 | Jonientz et al. |
| 2007/0135756 | A1 | 6/2007 | Kohlbrenner et al. |
| 2012/0245515 | A1 | 9/2012 | Calasso et al. |
| 2013/0181538 | A1 | 7/2013 | Calasso et al. |
| 2014/0276583 | A1 | 9/2014 | Chen et al. |
| 2015/0246179 | A1* | 9/2015 | Zur ................. G16H 40/67 604/207 |
| 2016/0074587 | A1 | 3/2016 | Searle et al. |
| 2016/0331906 | A1 | 11/2016 | Harms et al. |
| 2016/0378951 | A1 | 12/2016 | Gofman et al. |
| 2018/0132990 | A1* | 5/2018 | Baeten ............... A61M 5/3202 |
| 2018/0238333 | A1* | 8/2018 | Jalali ................ A61M 60/419 |
| 2019/0175145 | A1* | 6/2019 | Schleicher ............ A61M 5/24 |
| 2020/0023137 | A1* | 1/2020 | Byerly .............. A61M 5/31568 |
| 2020/0246548 | A1* | 8/2020 | Bill ...................... G16H 20/17 |

FOREIGN PATENT DOCUMENTS

| | | | |
|---|---|---|---|
| EP | 1393764 | | 3/2013 |
| EP | 3042676 | | 7/2016 |
| EP | 3103492 | | 12/2016 |
| JP | 11304893 | A * | 11/1999 |
| JP | 2004-526486 | | 9/2004 |
| JP | 2007-506469 | | 3/2007 |
| WO | WO 1997/030742 | | 8/1997 |
| WO | WO 2002/043573 | | 6/2002 |
| WO | WO 02/064196 | | 8/2002 |
| WO | WO 2003/005891 | | 1/2003 |
| WO | WO 2003/047426 | | 6/2003 |
| WO | WO 2013/050535 | | 4/2013 |
| WO | WO 2014/161954 | | 10/2014 |
| WO | WO 2016/050902 | | 4/2016 |
| WO | WO 2016/142727 | | 9/2016 |
| WO | WO 2017/032586 | | 3/2017 |

OTHER PUBLICATIONS

PCT International Preliminary Report on Patentability in International Appln. No. PCT/EP2018/085389, dated Jun. 23, 2020, 8 pages.

PCT International Search Report and Written Opinion in International Appln. No. PCT/EP2018/085389, dated Mar. 26, 2019, 11 pages.

* cited by examiner

DRUG DELIVERY DEVICE WITH NON-CONTACT SENSOR

CROSS REFERENCE TO RELATED APPLICATIONS

The present application is the national stage entry of International Patent Application No. PCT/EP2018/085389, filed on Dec. 18, 2018, and claims priority to Application No. EP 17306871.9, filed on Dec. 21, 2017, the disclosures of which are incorporated herein by reference.

TECHNICAL FIELD

The present disclosure relates to a drug delivery device with a non-contact sensor for measuring a dose of medicament ejected from the drug delivery device, and in particular to an apparatus including a generator sensor in which the power generated is also the sensed signal.

BACKGROUND

A variety of diseases exists that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning a dose setting dial and observing the actual dose from a dose window or display of the insulin pen. The dose is then injected by inserting the needle into a suited skin portion and pressing the dose setting dial or an injection button of the insulin pen. To be able to monitor insulin injection, for instance to prevent false handling of the insulin pen or to keep track of the doses already applied, it is desirable to measure information related to a condition and/or use of the injection device, such as for instance information on the injected insulin dose.

In some previous injection devices with electronic monitoring means, a wake-up switch is provided in the dose dialing button or is connected to the dose dialing button. In such devices, the electronic monitoring means are powered on when the user depresses the dose dialing button to dispense the dose. However, in such devices, the wake-up signal is received at the same moment as the dose dispensing begins, which leads to a reduction in reliability and the possibility that the dispensed dose may not be accurately recorded. On the other hand, if the electronic monitoring means are always on, so that the beginning of the dose dispensing operation is certain to be observed, then a relatively high amount of power is consumed, and the battery of the injection device may be drained before it is used. Alternatively, the battery supplied with the injection device would need to be very much larger than would otherwise be necessary.

SUMMARY

A first concept disclosed herein is a drug delivery device including a magnet assembly comprising a plurality of magnets arranged in a ring, wherein each magnet is arranged so that its polarity is opposite to each adjacent magnet, a coil assembly comprising one or more coils, wherein the magnet assembly and the coil assembly are arranged to rotate relative to each other during ejection of medicament from the drug delivery device such that a voltage signal is produced in the coil assembly when a unit of dose is ejected, and processing circuitry arranged to receive the voltage signal, increment a counter in response to receipt of the voltage signal, and store information indicative of the number of units of dose ejected during a medicament ejection.

The magnet assembly may be supported on, or may be integral with, a first rotatable component of the drug delivery device, and the coil assembly may be supported on, or may be integral with, a second rotatable component of the drug delivery device.

The first rotatable component of the drug delivery device may be a dose setting dial and the second rotatable component of the drug delivery device may be a dial sleeve.

The first rotatable component of the drug delivery device may be a dial sleeve and the second rotatable component of the drug delivery device may be a dose setting dial.

The magnet assembly may further comprise a Ferromagnetic retaining ring and the plurality of magnets may be secured to the Ferro-magnetic retaining ring.

Each of the one or more coils of the coil assembly may have a Ferro-magnetic core. The coil assembly may comprise a coil support ring made of a non-magnetic material. The coil assembly may comprise a plurality of coils spaced circumferentially around the coil support ring.

The coil support ring and the magnet assembly may be arranged parallel to each other. The coil support ring and the magnet assembly may be arranged concentrically. The magnet assembly and the coil assembly may have a common rotation axis extending in a longitudinal direction.

Each of the one or more coils of the coil assembly may be axisymmetric about the common rotation axis.

Each of the one or more coils of the coil assembly may be parallel with the common rotation axis.

The polarity of the magnets may be parallel with the common rotation axis. Alternatively, the polarity of the magnets may be perpendicular to the common rotation axis.

The processing circuitry may be configured to wake-up in response to receiving the voltage signal and the voltage signals may provide the power required by the processing circuitry to increment the counter and to store the information indicative of the number of units of dose ejected during the medicament ejection.

The drug delivery device may further include a passive electric circuit configured to shape the voltage signal before it is received by the processing circuitry. The passive electric circuit may include a transformer configured to step up the voltage of the voltage signal.

BRIEF DESCRIPTION OF THE FIGURES

Example embodiments will now be described with reference to the accompanying figures, of which.

DETAILED DESCRIPTION

In the following disclosure, embodiments will be described with reference to an insulin injection device. The present disclosure is however not limited to such application and may equally well be deployed with drug delivery devices that eject other medicaments.

Figure 1:
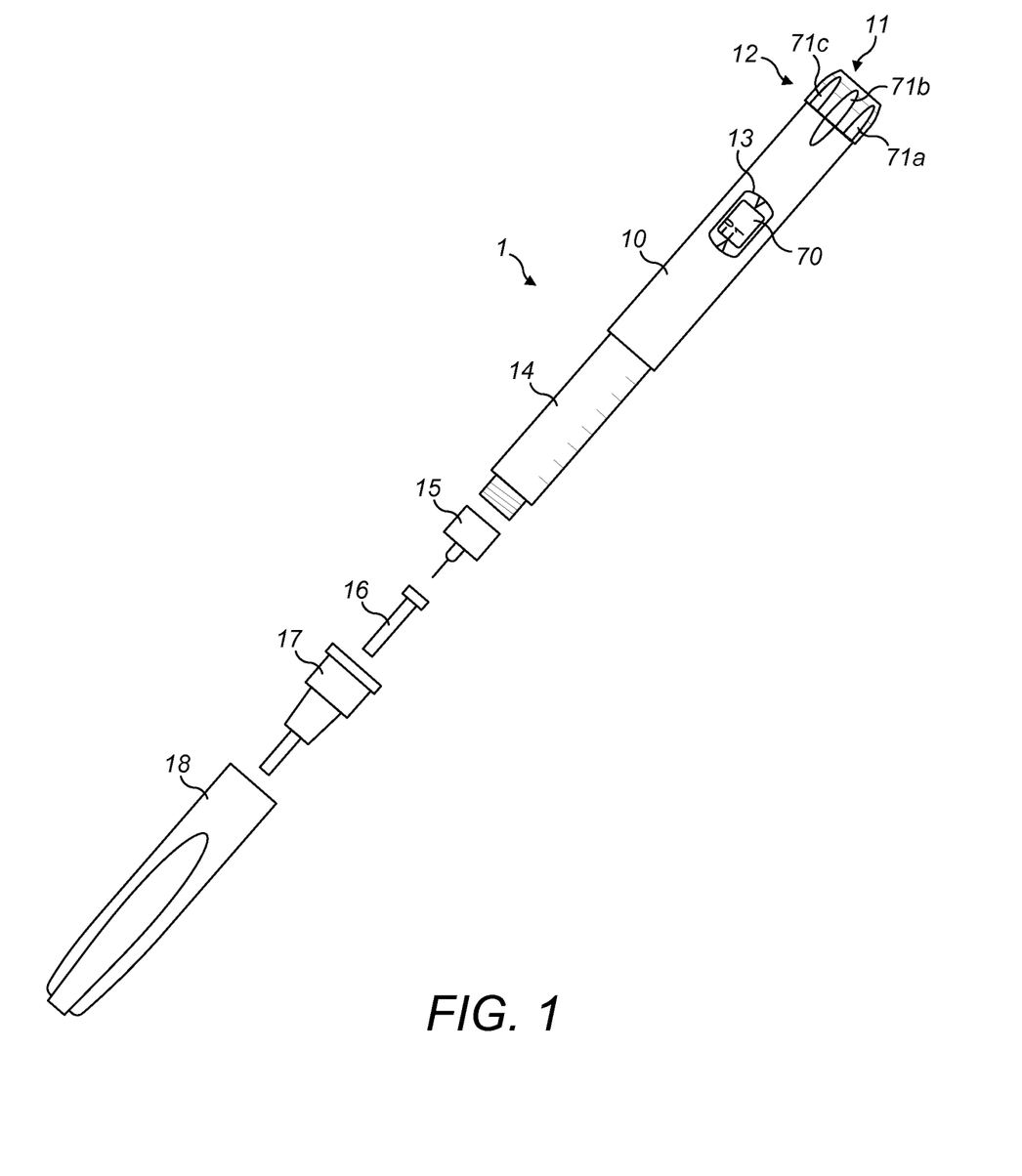
FIG. 1 shows an exploded view of an injection device.

FIG. 1 is an exploded view of a medicament administration device. In this example, the medicament administration device is an injection device 1, such as Sanofi's AllStar® insulin injection pen or Sanofi's SoloStar® insulin injection pen, however the present disclosure is also compatible with other types and makes of injection pens as described below. The present disclosure is also compatible with other types of drug delivery devices such as needless injectors.

The injection device 1 of FIG. 1 is a pre-filled injection pen that comprises a housing 10 and contains an insulin container 14, to which a needle 15 can be affixed. The injection device 1 may be disposable or re-usable. The needle is protected by an inner needle cap 16 and either an outer needle cap 17 or an alternative cap 18. An insulin dose to be ejected from injection device 1 can be programmed, or 'dialed in' by turning a dose setting dial 12 (also referred to herein as a dose selection element 12), and a currently programmed dose is then displayed via dosage window 13, for instance in multiples of units. For example, where the injection device 1 is configured to administer human insulin, the dosage may be displayed in so-called International Units (IU), wherein one IU is the biological equivalent of about 45.5 micrograms of pure crystalline insulin (1/22 mg). Other units may be employed in injection devices for delivering analogue insulin or other medicaments.

The dosage window 13 may be in the form of an aperture in the housing 10, which permits a user to view a limited portion of a number sleeve 70 that is configured to move when the dose setting dial 12 is turned, to provide a visual indication of a currently programmed dose. It should be noted that the selected dose may equally well be displayed differently than as shown in the dosage window 13 in FIG. 1. For example, only every second dose unit may be shown, due to space restrictions on the number sleeve 70. The un-numbered dose units may be represented by tick marks between the displayed numerals. Alternatively, the number sleeve 70 may remain stationary during the dose dialing phase, and the dosage window 13 may move as a dose is dialed in to reveal the number corresponding to the dialed dose. In either case, the number sleeve 70 may be a component which rotates when a dose is being dispensed from the injection device 1.

In this example, the dose setting dial 12 includes one or more formations 71a, 71b, 71c that facilitate programming because they improve the grip a user feels when grasping the dose setting dial 12. In another example (not shown) the dose setting dial does not include formations.

The injection device 1 may be configured so that turning the dose setting dial 12 causes a mechanical click sound to provide acoustical feedback to a user. The number sleeve 70 mechanically interacts with a piston in insulin container 14.

When needle 15 is stuck into a skin portion of a patient, and then injection button 11 is pushed, the insulin dose displayed in dosage window 13 will be ejected from injection device 1. When the needle 15 of injection device 1 remains for a certain time in the skin portion after the injection button 11 is pushed, a high percentage of the dose is actually injected into the patient's body. Ejection of the insulin dose may also cause a mechanical click sound, which is however different from the sounds produced when using dose setting dial 12. In some other embodiments, the injection device 1 does not have a separate injection button 11 and a user depressed the entire dose setting dial 12, which moves longitudinally relative to the housing 10, in order to cause the medicament to be dispensed.

In the various embodiment, during delivery of the insulin dose, the dose setting dial 12 is turned to its initial position in an axial movement, that is to say without rotation, while the number sleeve 70 is rotated to return to its initial position, e.g. to display a dose of zero units.

Injection device 1 may be used for several injection processes until either the insulin container 14 is empty or the expiration date of the medicament in the injection device 1 (e.g. 28 days after the first use) is reached.

Furthermore, before using injection device 1 for the first time, it may be necessary to perform a so-called "prime shot" to remove air from insulin container 14 and needle 15, for instance by selecting two units of insulin and pressing injection button 11 while holding injection device 1 with the needle 15 upwards. For simplicity of presentation, in the following, it will be assumed that the ejected doses substantially correspond to the injected doses, so that, for instance the number of medicament dose units ejected from the injection device 1 is equal to the number of medicament dose units received by the user. Nevertheless, differences (e.g. losses) between the ejected amounts and the injected doses may need to be taken into account.

Figure 2:
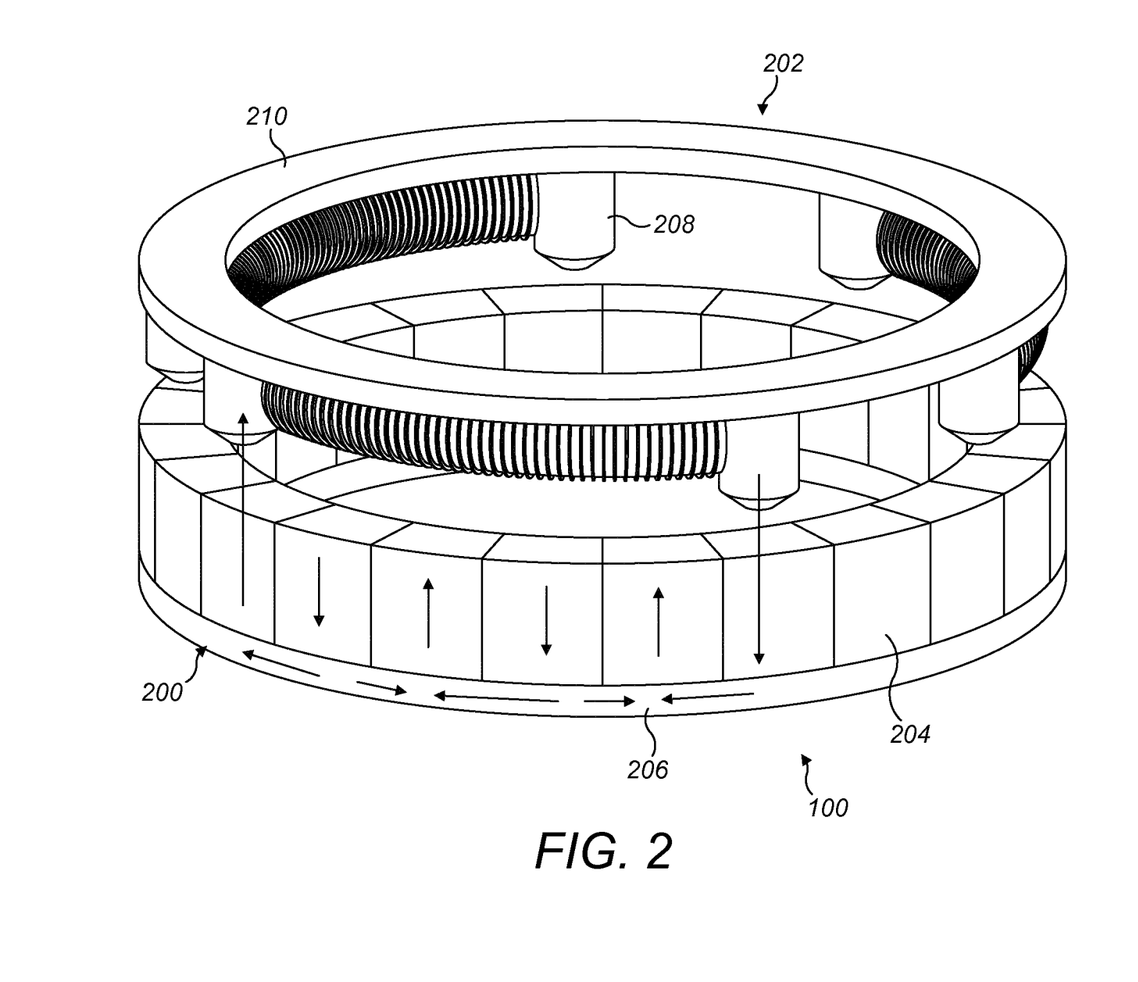
FIG. 2 shows internal components of the injection device of FIG. 1, forming a contactless sensor.
Figure 3:
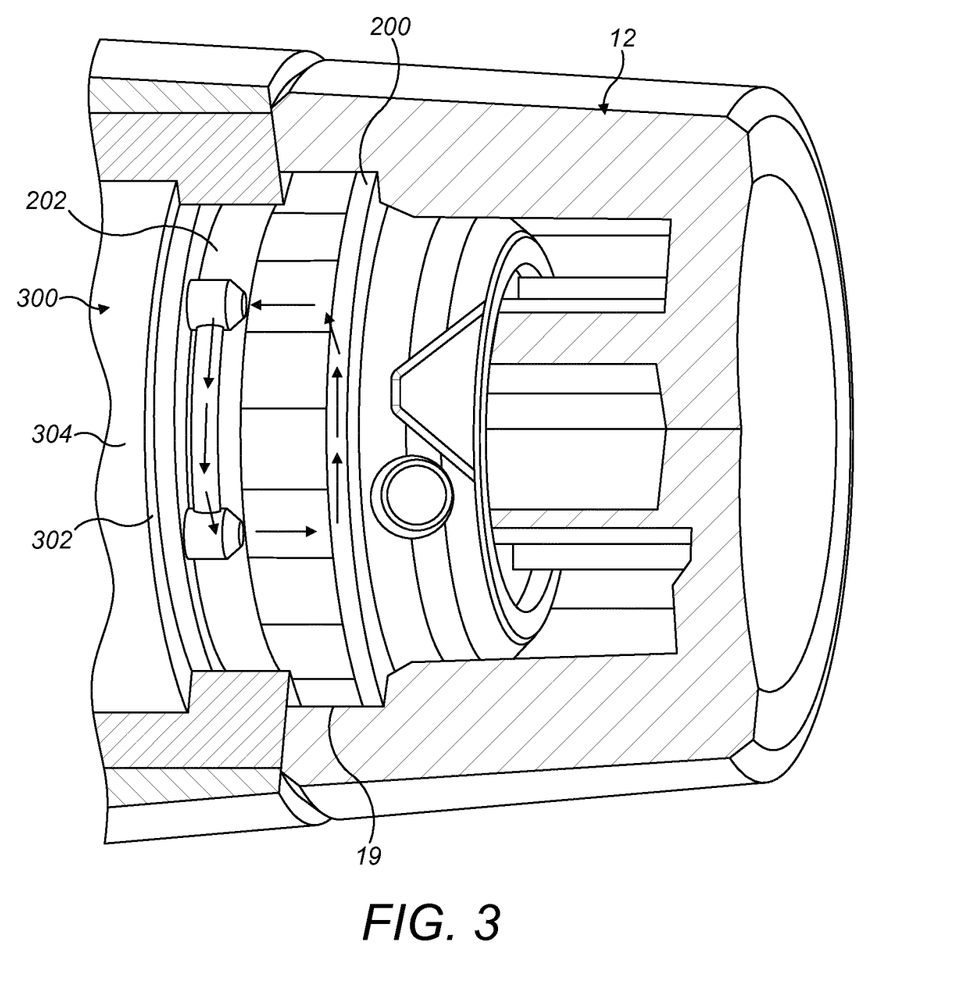
FIG. 3 shows the internal components of FIG. 2 in situ within the injection device.

FIG. 2 illustrates internal components of the injection device 1 forming a contactless sensor 100. The contactless sensor 100 may also be referred to herein as a passive sensor or powerless sensor. FIG. 3 shows the internal components of FIG. 2 in situ within the injection device 1. The lower part of FIG. 2 is a magnet assembly 200, while the upper part is a coil assembly 202. The magnet assembly 200 comprises a plurality of magnets 204 arranged in a ring. Each magnet 204 is arranged so that its polarity is opposite to the adjacent magnet in the ring. This assembly produces a spatially varying magnetic field which varies periodically along the circumference of the ring. In the embodiment depicted the magnet assembly 200 comprises 24 magnets. This corresponds to the number of dose units which are dialed into the injection device 1 by one complete revolution of the dose setting dial 12. However, any suitable number of magnets 204 may be used. The magnet assembly 200 also comprises a retaining ring 206. The retaining ring 206 is made of a Ferro-magnetic material.

The coil assembly 202 comprises at least one coil 208. In the embodiment depicted, the coil assembly 202 comprises three coils 208 spaced equally in a ring. However, any suitable number of coils may be used. The coils 208 are, for example, cylindrical coils of wire. The coil assembly 202 also comprises a coil support ring 210. The coil support ring 210 is made of a non-magnetic material. Each coil 208 also comprises a Ferro-magnetic core. The ends of this Ferro-magnetic core may extend beyond the ends of the coil 208 to secure the coil 208 to the coil support ring 210. The arrows in FIG. 2 show the direction of the magnetic field in the magnets 204, Ferro-magnetic retaining ring 206 and coil 208. The retaining ring 206 and coil support ring 210 are arranged parallel to each other, i.e. in the same plane. The magnets 204 are supported on an inner side of the retaining ring 206 and the one or more coils 208 are supported on an inner side of the coil support ring 210, such that the magnets and coils are adjacent one another.

When the coils 208 move relative to the magnets 204, a magnetic flux flows through the coils 208. The magnetic flux flowing through the coils 208 varies periodically with the spatially varying magnetic field produced by the magnet assembly 200. This variation in time produces a voltage difference at the ends of the coil 208. The voltage output (EMF) is proportional to the rate of change of the magnetic flux and in effect it is proportional to the relative angular velocity of the two assemblies (200, 202). Consequently, the rate of change in magnetic field as the magnet assembly 200 rotates relative to the coil assembly 202 can be measured with the coil assembly 202.

The magnet assembly 200 and coil assembly 202 are retained within the housing of an injection device 1. Locations within the injection device 1 are chosen which exhibit relative movement when doses are being injected. In some examples, providing an additional switch or trigger which activates the sensor during drug delivery allows the contactless sensor 100 to distinguish between dialing and delivery. This allows further locations within the injection device, where relative movement between the two assemblies (200, 2020) exists while dialing in a dose, to be used.

The injection device 1 also houses processing circuitry (not shown) for receiving the signals generated in the coil assembly 202 and determining the injected dose. The processing circuitry may comprise a passive analog circuit. For ease of wiring, the processing circuitry is located on the same part of the injection device 1 as the coil assembly 202.

FIG. 3 shows an embodiment of the magnet assembly 200 and coil assembly 202 in situ within the injection device 1. In this example, the magnet assembly 200 is supported in the dose setting dial 12, for example on the inner circumferential surface 19 of the dose setting dial. The coil assembly 202 is supported on the dial sleeve 300, for example on an outer circumferential surface 304 of the dial sleeve 300, or a distal end 302 of the dial sleeve 300. The dial sleeve 300 may be integral with, or secured to, the number sleeve 70. The dial sleeve 300 is a component having a distal end 302 close to the dose setting dial 12 and which rotates relative to the dose setting dial 12 during dose ejection, but not during dose dialing. The coil assembly 202 may be supported at or near the distal end 302 of the dial sleeve 300. In operation the dose setting dial 12 is configured to move axially relative to the main body 10 and dial sleeve 300 of the injection device 1 by a short distance. This movement occurs when a user exerts a force on the end of the dose setting dial 12. This movement disengages an internal clutch (not shown) and allows the dial sleeve 300 and other internal components of the injection device 1 to rotate relative to the dose setting dial 12. FIG. 3 shows the components during dose delivery, i.e. when the dose setting dial 12 has been depressed. This brings the magnet assembly 200 and the coil assembly 202 closer together.

FIGS. 2 are 3 show the magnets 204 being attached to the Ferro-magnetic retaining ring 206. The Ferro-magnetic retaining ring 206 decreases leakage of magnetic field to the surrounding, thus increasing the magnetic circuit's efficiency and reducing substantially the magnetic field surrounding the sensor, i.e. the ring serves as a channel in which the magnetic field flows. The coil support ring 210 which holds the coils in place is of a non-magnetic material in order not to interfere with the desired flow of the magnetic field. In these embodiments, the core of each coil 208 is made of a Ferro-magnetic material. It is located within the coil and its ends bulge out of it in the direction of the magnetic circuit. Being Ferro-magnetic allows the core to direct the magnetic field, produced by the magnets near its ends, to flow through it. As in the 270 case of the Ferro-magnetic retaining ring 206, the Ferro-magnetic core increases the magnetic field flowing through the coils thus increasing the efficiency of the magnetic circuit, and decreasing the magnetic field outside the sensor.

Due to the Ferro-magnetic core of the coil 208, there is an attraction between the coil assembly 202 and the magnet assembly 200 in the axial and tangential direction. The attraction varies periodically with the location of the magnet assembly 200 relative to the coils 208. In some embodiments, the coil assembly 202 has an axisymmetric arrangement with respect to the rotation axis, and in this way the magnetic attraction will create a pure moment on the axis of rotation. If the symmetry is not kept an added force will be applied on the sensor and therefore to the force required to rotate the dose setting dial 12. The tangential attraction moment creates an effect similar to a ratchet; it forces the magnet assembly 200 to rest at specific angular coordinates. In some embodiments, a complete rotation of the dose setting dial 12 corresponds to 24 dose units, and consequently the magnet assembly 200 comprises 24 magnets 204. The ratchet effect of the tangential attraction moment is therefore in sync with the injected doses. This effect may allow the removal of a mechanical ratchet mechanism between the dose setting dial 12 and dial sleeve 300. It should be noted that the sensor can still work without the Ferro-magnetic core of the coil 208. The efficiency of the sensor is decreased, but the attraction forces between the two assemblies are removed.

In some alternative embodiments the positions of the magnet assembly 200 and coil assembly 202 may be reversed, such that the coil assembly 202 is supported in the dose setting dial 12 and the magnet assembly 200 is supported on the dial sleeve 300. The only significant change required for this arrangement is that the processing circuitry is located in the dose setting dial 12, rather than on the dial sleeve 300.

Figure 4:
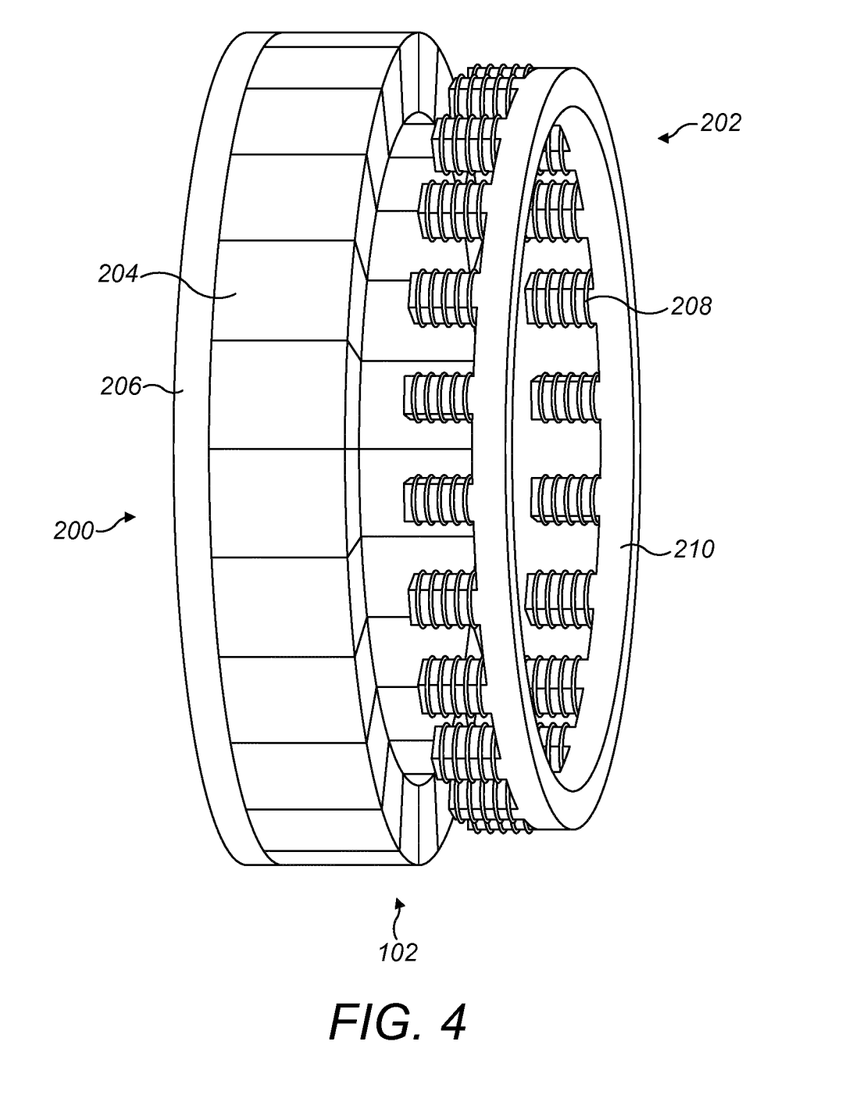
FIG. 4 shows internal components of the injection device of FIG. 1 forming a contactless sensor according to some other embodiments.

Additional designs for both the magnet assembly 200 and coil assembly 202 are possible. FIG. 4 illustrates internal components of the injection device 1 forming a contactless sensor 102 according to some other embodiments. The design of FIG. 4 is particularly useful where a non Ferro-magnetic core is used in the coils 208, or where no core is used. In FIG. 4, the coil support ring 210 supports the same number of coils 208 as there are magnets 204 in the magnet assembly 200. For example, where the magnet assembly 200 has 24 magnets 204, the coil assembly 202 has 24 coils. The coils 208 are equally spaced and therefore have the same spacing as the magnets 204. However, the coil assembly 202 could have fewer coils, for example 12 or 6 equally spaced coils could be used. The spacing between the coils 208 should align with the periodicity of the magnets 204 in the magnet assembly 200.

Figure 5:
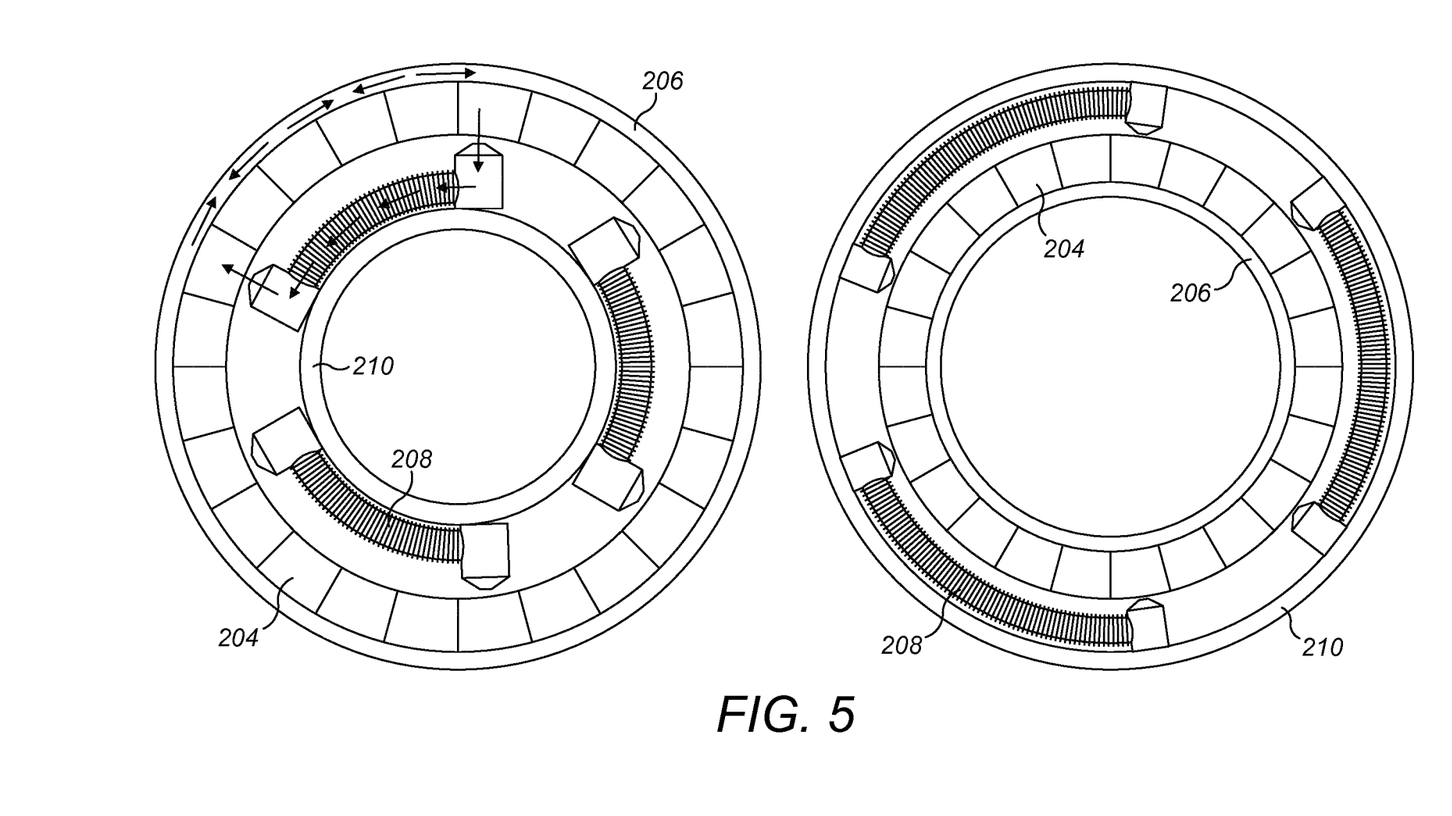
FIG. 5 shows two additional designs of the contactless sensor, having a radial configuration.

FIG. 5 shows two additional designs of the magnet assembly 200 and coil assembly 202, having a radial configuration, i.e. the polarization of the magnets 204 is in the radial direction. The left hand figure shows a configuration where the magnet assembly 200 forms an outer ring while the coil assembly 202 forms an inner ring. The magnet assembly 200 and coil assembly 202 are arranged concentrically. The Ferro-magnetic retaining ring 206 forms the outermost ring and may be secured to the inner surface of the dose setting dial 12, while the magnets 204 are supported on the inner circumference of the Ferro-magnetic retaining ring 206. The coil assembly 202 is located inside the magnet assembly 200. The coil support ring 210 forms the innermost ring and may be secured to the outer surface of the dial sleeve 300, while the coils 208 are supported on the outer circumference of the coil support ring 210. The arrows in the left hand figure show the magnetic circuit flow.

In the right hand Figure, the positions of the magnet assembly 200 and coil assembly 202 are reversed. The coil support ring 210 forms the outermost ring and may be secured to the inner surface of the dose setting dial 12, while the coils 208 are supported on the inner circumference of the coil support ring 210. The magnet assembly 200 is located inside the coil assembly 202. The Ferro-magnetic retaining ring 206 forms the innermost ring and may be secured to the outer surface of the dial sleeve 300, while the magnets 204 are supported on the outer circumference of the Ferro-magnetic retaining ring 206.

These embodiments may be more appropriate for some injection device designs where space is available in the radial direction. These designs do not require any extension of the injection device dimensions in the axial direction. An enlargement of the diameter of the injection device 1 may be required to the dose setting dial 12 end.

Figure 6:
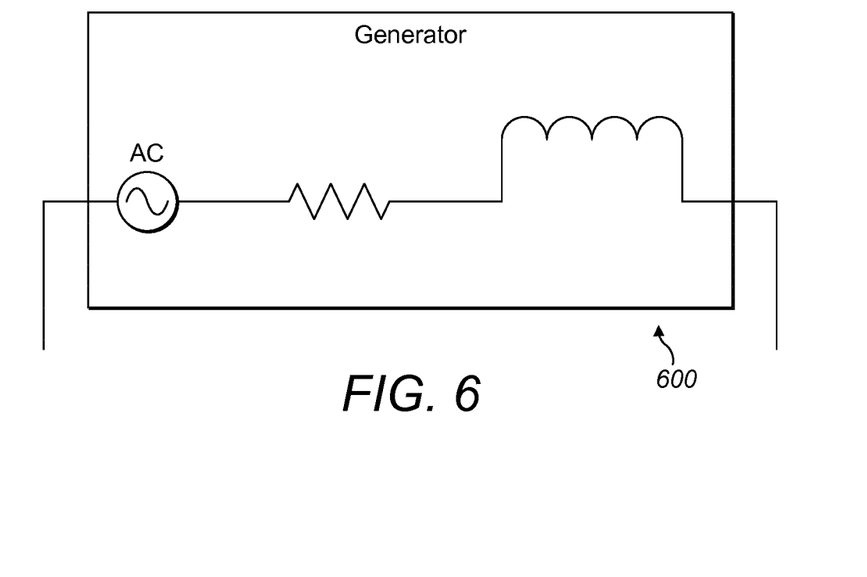
FIG. 6 shows an example of a generator model forming part of processing circuitry.

FIG. 6 illustrates an example of a generator model 600 forming part of the processing circuitry. As long as the circuit is open no current flows, therefore the voltage output depends only on the EMF. The generator model 600 represents the internal resistance and impedance of the coils and connected processing circuitry and the action of the periodically varying magnetic field.

For the design of the magnetic assembly 200 shown in FIGS. 2, 4 and 5, the magnetic flux varies in an almost sinusoidal manner along the circumference of the magnet ring. The periodicity of the magnetic field is set to complete a single cycle for every dose unit injected, thus creating a voltage extremum with every injected dose unit. Every time the ends of the coils 208 pass the boundary between two magnets 204, are voltage pulse is generated, allowing the number of dose units ejected to be counted. The voltage signal may also provide the power necessary for a microprocessor or other processing unit to perform the counting. For example, the microprocessor may operate in a very low power state or be in an off state. The microprocessor may be configured to activate or turn on when it receives a voltage signal of a predetermined strength. The voltage signal may provide enough power for the microprocessor to run for a few milliseconds, but this is enough for the microprocessor to count the voltage pulse, for example by incrementing a counter in a permanent memory portion of the processing circuitry. Thus the processing circuitry may operate as a powerless sensor system for the injection device 1.

The processing circuitry may then store information indicative of the number of units of dose delivered during a drug delivery operation. Thus, the stored information indicative of the number of units of dose delivered during the drug delivery operation is based upon the process of incrementing the counter. The stored information may be retrieved from the memory of the injection device 1 using an external computing device. The external computing device may provide the power necessary for reading the memory, for example using NFC technology. The injection device may alternatively or in addition contain a small battery for powering the data retrieval. The injection device 1 may also comprise a display and a battery for displaying the dose history information. The display may use a low power technology, such as E ink.

Different designs in terms of the coil size, magnet strength and relative positioning of the magnet and coil assemblies will produce different voltage outputs and different noise levels. In cases where the peak voltage output is not high enough to trigger the microprocessor an analog transformer can be added to the sensor, which will step-up the EMF output. Where unacceptable levels of noise are present, bandpass analog filtering can be used to filter out unnecessary information. The bandpass may be chosen specifically for a particular generator design.

In some injection device designs, a ratchet mechanism exists between the dose setting dial 12 and the dial sleeve 300. This ratchet creates a ticking sound for each dose unit injected. Due to the ratchet mechanism the dial sleeve turns 300 in a non-constant manner during dose ejection. When the tooth of the ratchet is passed, the relative angular velocity between the dose setting dial 12 and the dial sleeve 300 peaks for a brief moment. This needs to be accounted for when calculating the voltage output. The initial relative angular orientation between the two assemblies may therefore be tuned so that the peak of velocity occurs when the coil assembly 202 experiences the maximum gradient in the magnetic field. Such tuning will optimize the voltage output of the sensor.

Some measurements have been performed using Sanofi's AllStar® insulin injection pen in order to assess the peak angular velocity of the dial sleeve during dose dispensing. A range in peak velocities of 5 to 25 rad/sec was observed. In order to ensure that the microprocessor is activated and that the dose unit is counted every time, the lowest peak velocity value should be used.

Figure 7:
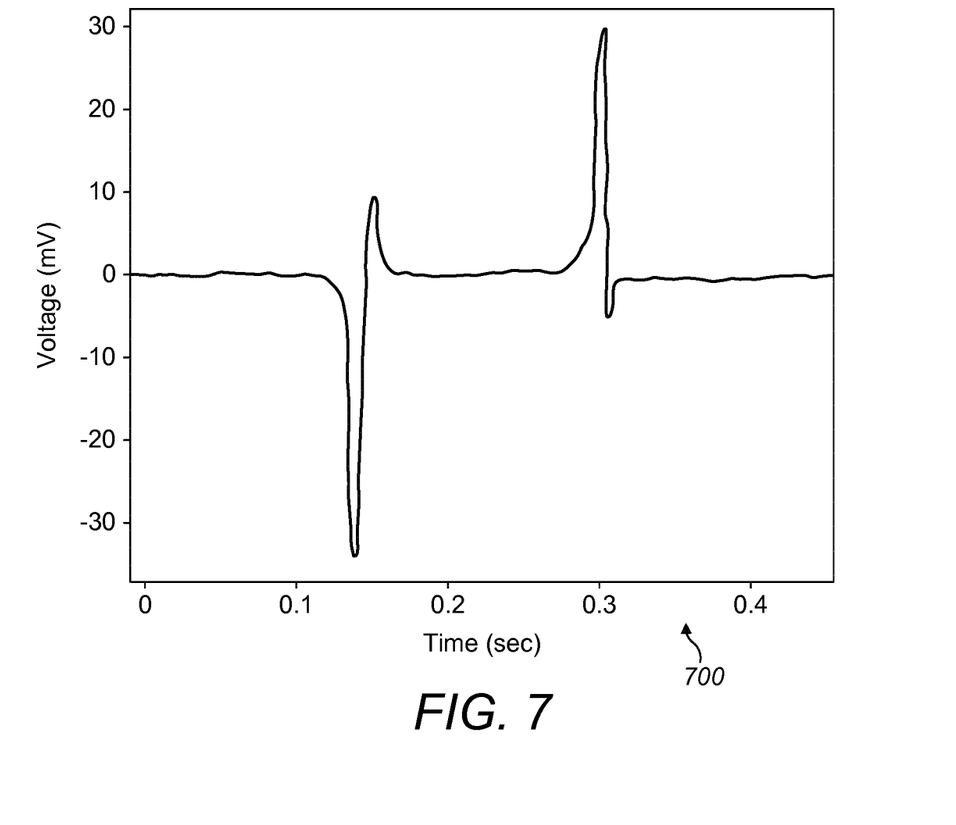
FIG. 7 shows the EMF signal generated in the contactless sensor for a particular sensor design.

FIG. 7 shows a simulation 700 of the EMF signal generated in the coils 208 for a particular generator design and using the lower value for peak velocity of 5 rad/sec.

The voltage peaks shown in FIG. 7 can be used to activate the microprocessor and count the injected dose units. The maximum voltage produced may be further increased by optimisation of the generator design for a particular scenario or injector design.

Figure 8:
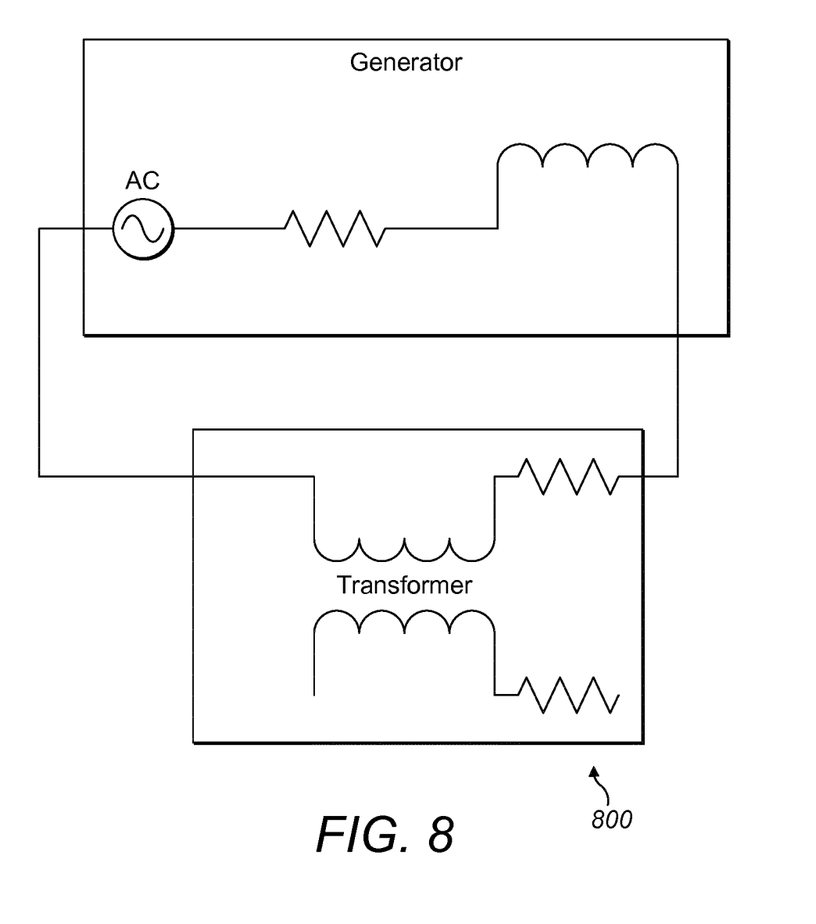
FIG. 8 shows a further model of a generator forming part of the processing circuitry, including a transformer.

In some other embodiments, the minimum threshold voltage required to trigger the microprocessor may be set at approximately 300 mV, in order to be more confident of avoiding false positives due to noise. The results shown in FIG. 7 exhibit a maximum voltage of only 30 mV. Consequently, in these embodiments a transformer is needed in order to step-up the voltage output. FIG. 8 shows a further model 800 of a generator forming part of the processing circuitry, including a transformer. When a transformer is connected, current flows through the circuit and therefore voltage drops occur due to internal impedance of the generator and transformer. As a result the voltage output changes. The main contributor to the change of voltage output is the transformer's resistance, although the resistance of the generator also contributes.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Examples of pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a volume of a drug into a human or animal body. The volume can typically range from about 0.5 ml to about 10 ml. Without limitation, the drug delivery device may include a syringe, needle safety system, pen injector, auto injector, large-volume device (LVD), pump, perfusion system, or other device configured for subcutaneous, intramuscular, or intravascular delivery of the drug. Such devices often include a needle, wherein the needle can include a small gauge needle (e.g., greater than about 24 gauge, and including 27, 29, or 31 gauge).

In combination with a specific drug, the presently described devices may also be customized in order to operate within required parameters. For example, within a certain time period (e.g., about 3 to about 20 seconds for injectors, and about 5 minutes to about 60 minutes for an LVD), with a low or minimal level of discomfort, or within certain conditions related to human factors, shelf-life, expiry, biocompatibility, environmental considerations, etc. Such variations can arise due to various factors, such as, for example, a drug ranging in viscosity from about 3 cP to about 50 cP.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis.

Examples of drugs for the treatment and/or prophylaxis of diabetes mellitus or complications associated with diabetes mellitus include an insulin, e.g., human insulin, or a human insulin analogue or derivative, a glucagon-like peptide (GBP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Examples of insulin analogues are Gly(A21), Arg(B31), Arg(B32) human insulin (insulin glargine); Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin; B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GBP-1, GBP-1 analogues and GBP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An examples of oligonucleotide is, for example: mipomersen/Kynamro, a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present concept include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immuno-pharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (such as, for example, adjustments, additions, or removals) of various components of the substances, formulations, apparatuses, methods, systems, devices, and embodiments described herein may be made without departing from the full scope and spirit of the present inventive concepts, which encompass such modifications and any equivalents thereof.

The invention claimed is:

1. A drug delivery device comprising:
   a magnet assembly comprising a plurality of magnets arranged in a ring, wherein each magnet is arranged to have a respective polarity opposite to each adjacent magnet polarity;
   a coil assembly comprising a coil support ring made from a non-magnetic material and one or more coils, each of the one or more coils comprising a Ferro-magnetic core extending beyond ends of each of the one or more coils to secure the one or more coils to the coil support ring, wherein the magnet assembly and the coil assembly are arranged to rotate relative to each other during ejection of medicament from the drug delivery device such that a voltage signal is produced in the coil assembly when a unit of dose is ejected; and
   a processing circuitry configured to:
      receive the voltage signal,
      increment a counter in response to receipt of the voltage signal, and
      store information indicative of a number of units of dose ejected during the medicament ejection.

2. The drug delivery device of claim 1, wherein the magnet assembly is supported on, or is integral with, a first rotatable component of the drug delivery device, and wherein the coil assembly is supported on, or is integral with, a second rotatable component of the drug delivery device.

3. The drug delivery device of claim 2, wherein the first rotatable component of the drug delivery device is a dose setting dial and the second rotatable component of the drug delivery device is a dial sleeve.

4. The drug delivery device of claim 2, wherein the first rotatable component of the drug delivery device is a dial sleeve and the second rotatable component of the drug delivery device is a dose setting dial.

5. The drug delivery device of claim 1, wherein the magnet assembly further comprises a Ferro-magnetic retaining ring and wherein the plurality of magnets are secured to the Ferro-magnetic retaining ring.

6. The drug delivery device of claim 1, wherein the one or more coils of the coil assembly comprise a plurality of coils spaced circumferentially around the coil support ring.

7. The drug delivery device of claim 1, wherein the coil support ring and the magnet assembly are arranged parallel to each other.

8. The drug delivery device of claim 1, wherein the coil support ring and the magnet assembly are arranged concentrically.

9. The drug delivery device of claim 1, wherein the magnet assembly and the coil assembly have a common rotation axis extending in a longitudinal direction.

10. The drug delivery device of claim 9, wherein each of the one or more coils of the coil assembly is axisymmetric about the common rotation axis.

11. The drug delivery device of claim 9, wherein each of the one or more coils of the coil assembly is parallel with the common rotation axis.

12. The drug delivery device of claim 9, wherein the polarity of the plurality of magnets is parallel with the common rotation axis.

13. The drug delivery device of claim 9, wherein the polarity of the plurality of magnets is perpendicular to the common rotation axis.

14. The drug delivery device of claim 1, wherein the processing circuitry is configured to wake-up in response to receiving the voltage signal.

15. The drug delivery device of claim 14, wherein the voltage signal provides power required by the processing circuitry to increment the counter and to store the information indicative of the number of units of dose ejected during the medicament ejection.

16. The drug delivery device of claim 1, further comprising a passive electric circuit configured to shape the voltage signal before the voltage signal is received by the processing circuitry.

17. The drug delivery device of claim 16, wherein the passive electric circuit comprises a transformer configured to step up a voltage of the voltage signal.

18. The drug delivery device of claim 1, wherein the processing circuitry comprises a bandpass analog filter configured to filter out unnecessary information from the information indicative of the number of units of dose ejected during the medicament ejection.

* * * * *